United States Patent [19]

McReynolds

[11] 3,957,262
[45] May 18, 1976

[54] HEAD SUPPORTING AND IMMOBILIZING DEVICE

[76] Inventor: William U. McReynolds, 2301 York St., Quincy, Ill. 62301

[22] Filed: Nov. 25, 1974

[21] Appl. No.: 526,534

[52] U.S. Cl. ............................ 269/328; 5/327 B; 297/391
[51] Int. Cl.² ......................................... A61G 13/00
[58] Field of Search ............ 269/328; 297/391, 408, 297/410; 128/134; 5/327 B

[56] References Cited
UNITED STATES PATENTS

| | | | |
|---|---|---|---|
| 1,971,624 | 8/1934 | Rusk | 269/328 |
| 2,169,117 | 8/1939 | Utermohlen | 5/327 B |
| 2,535,559 | 12/1950 | Wolf | 269/328 |
| 2,846,942 | 8/1958 | Bowman | 297/408 X |
| 3,099,441 | 7/1963 | Ries | 269/328 |
| 3,188,079 | 6/1965 | Boetcker | 269/328 |
| 3,216,767 | 11/1965 | Lutfy | 297/391 |
| 3,319,954 | 5/1967 | Sheuich | 269/328 |
| 3,672,364 | 6/1972 | Raukin | 128/134 |
| 3,835,861 | 9/1974 | Kees | 269/328 X |

*Primary Examiner*—Harold D. Whitehead
*Attorney, Agent, or Firm*—Lee & Smith

[57] ABSTRACT

A device for supporting and immobilizing a patient's head during surgery or examination by a treating physician. The device includes a headpiece adapted to receive and approximate the contour of the patient's head, and means for securing the headpiece to one or more support members. The support members have upper ends for steadying a portion of the treating physician's upper limb and lower or base ends mounted to a surface for supporting the patient's body.

20 Claims, 5 Drawing Figures

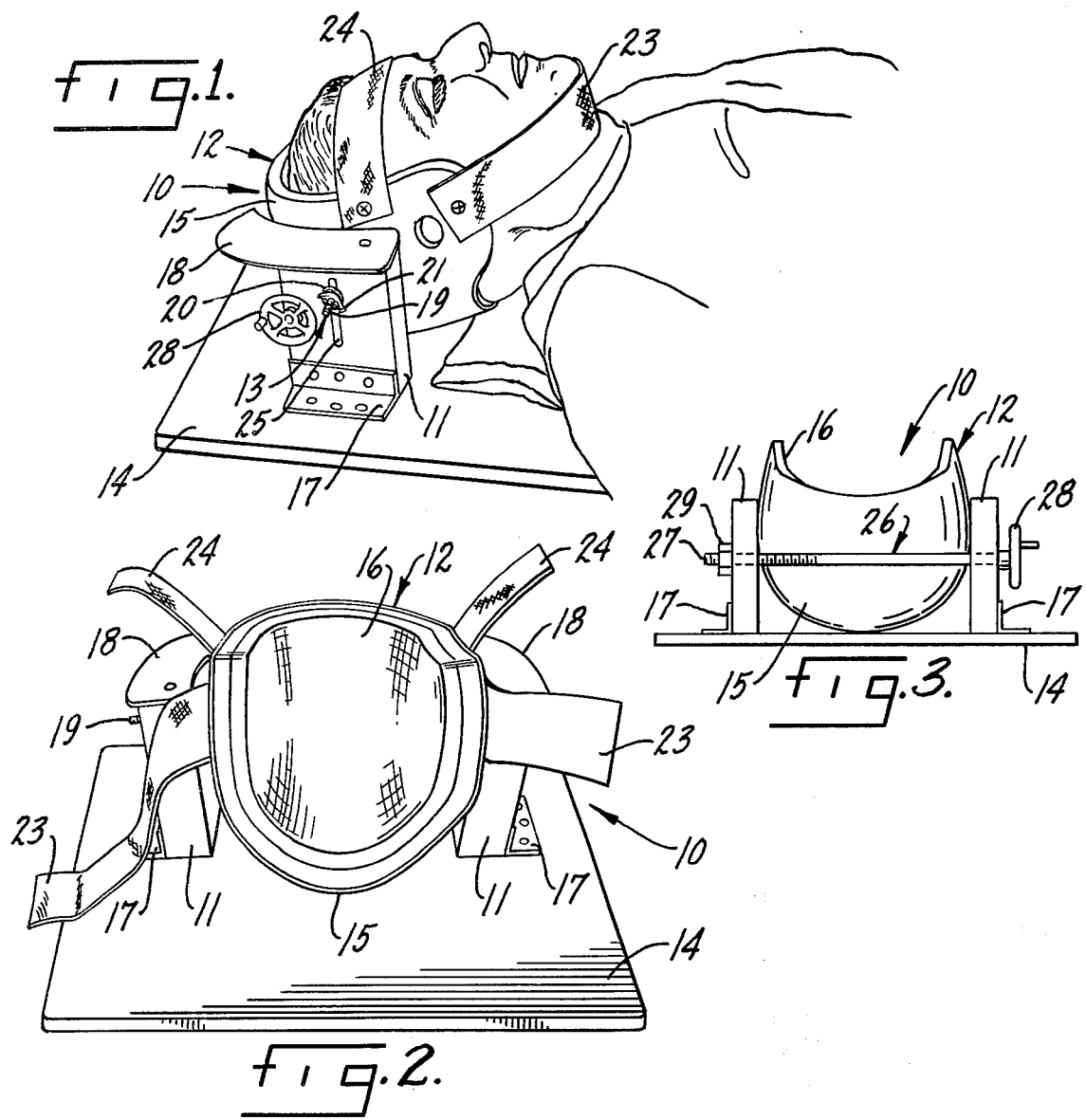
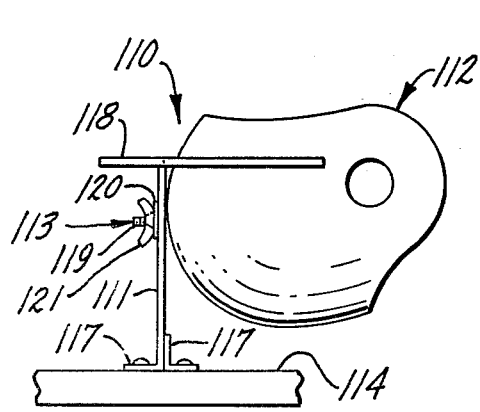
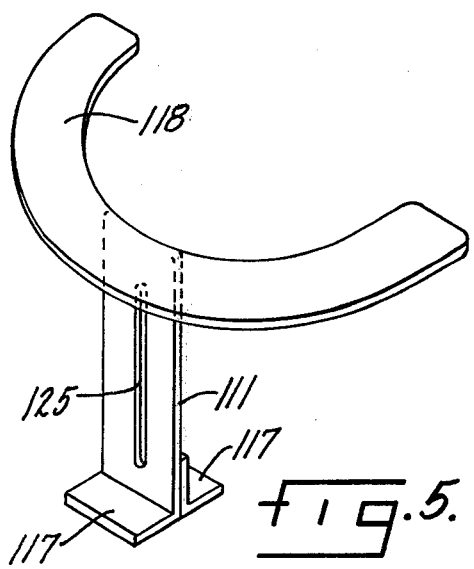

HEAD SUPPORTING AND IMMOBILIZING DEVICE

BACKGROUND OF THE INVENTION

This invention relates to a head supporting and immobilizing device and more particularly, to a device suitable for supporting and immobilizing a patient's head during surgery or examination by a treating physician.

During many types of surgery and examination involving the head and face, the patient's head should be immobilized so that inadvertent motion does not interfere with the performance of delicate procedures by the treating physician. Since such procedures are often quite lengthy, the patient's head should also be supported in a comfortable position in which the patient can breath easily and avoid undue strain. In addition, a portion of the treating physician's upper limb should be steadied during the performance of such lengthy and delicate procedures.

In the past, devices for supporting and immobilizing a patient's head have taken many forms. For instance, a headrest for eye surgery is disclosed in U.S. Pat. No. 3,347,544. The headrest is constructed of foam rubber with a recess formed in the top surface to receive the patient's head. However, foam rubber headrests of this type have not proven to be satisfactory. While the recess in the foam rubber provides a degree of support, it does not immobilize the patient's head. The headrest disclosed in U.S. Pat. No. 3,369,548 has proven to be somewhat more satisfactory. It has a recess formed in the top surface to receive the patient's head and is less resilient than the foam rubber headrest disclosed in U.S. Pat. No. 3,347,544. As a result, it provides better support. However, it, too, does not immobilize the patient's head. Other patents disclosing headrests include U.S. Pat. Nos. 3,188,079; 3,650,523; and 3,672,364. However, none of the headrests disclosed in these patents has proven to be completely satisfactory for supporting and immobilizing a patient's head during the performance of delicate and lengthy surgery and examination.

SUMMARY OF THE INVENTION

With the present invention, a device for supporting and immobilizing a patient's head during surgery or examination by a treating physician is provided. The device includes one or more generally vertical support members. Each of the support members has an upper end for steadying a portion of the treating physician's upper limb and a lower end or base mounted to a surface for supporting the patient's body. A headpiece adapted to receive and approximate the contour of the patient's head is disposed above the support surface by means for securing the headpiece to the support members.

Accordingly, it is an object of the present invention to provide a device for supporting and immobilizing a patient's head during surgery or examination which overcomes the disadvantages of devices previously used for this purpose.

It is also an object of the present invention to provide a device for immobilizing a patient's head so that inadvertent motion does not interfere with the performance of delicate surgical or examinational procedures.

It is a further object of the present invention to provide a device for supporting a patient's head in a comfortable position so that the patient can breath easily and avoid undue strain during the performance of lengthy surgical or examinational procedures.

It is an additional object of the present invention to provide a device for steadying a portion of a treating physician's upper limb during the performance of lengthy and delicate surgical and examinational procedures.

These and other objects and advantages of the present invention will be set forth in greater detail below.

BRIEF DESCRIPTION OF THE DRAWINGS

FIG. 1 is a side perspective view illustrating the head supporting and immobilizing device of the present invention as it supports and immobilizes a patient's head.

FIG. 2 is a front perspective view illustrating the head supporting and immobilizing device of the present invention.

FIG. 3 is a rear elevation of the head supporting and immobilizing device of the present invention.

FIG. 4 is a side elevation of an alternative embodiment of the head supporting and immobilizing device of the present invention.

FIG. 5 is a perspective view of the support member of the alternative embodiment of the head supporting and immobilizing device of the present invention.

DESCRIPTION OF THE PREFERRED EMBODIMENT

The general nature of the preferred embodiment of the present invention may be understood by referring to FIGS. 1 through 3 in which the head supporting and immobilizing device 10 includes a pair of generally vertical and horizontally spaced support members 11, a headpiece 12 and means 13 for securing the headpiece 12 to the support members 11. The support members 11 have lower or base ends mounted to a surface 14 for supporting a patient's body and upper ends for steadying a portion of a physician's upper limb. The headpiece 12, which receives and approximates the contour of a patient's head, is disposed between the support members 11 and above the support surface 14. Means 13 secures the headpiece 12 to the support members 11 in any of various desired positions intermediate the upper and lower ends thereof.

Referring to FIGS. 1 and 2, the headpiece 12 is provided with a semi-rigid exterior 15. The exterior 15 is preferably constructed of a thin plastic material which has the characteristic of generally approximating the contour of the patient's head. The headpiece 12 also includes a padded interior 16. The interior 16 is preferably constructed of a soft foam rubber material which has the characteristic of closely conforming to the size and shape of the patient's head. When the patient uses the head supporting and immobilizing device 10, the semi-rigid exterior 15 and the padded interior 16 cooperate to support and immobilize the patient's head in the headpiece 12.

Referring to FIGS. 1 and 3, braces 17 are provided to rigidly mount the support members 11 to the support surface 14 and means 13 is provided to secure the headpiece 12 to the support members 11. Means 13 includes bolts 19, washers 20 and bolt receiving nuts 21. Bolts 19 pass through opposite side portions of the semi-rigid exterior 15 of the headpiece 12 and also pass through generally vertical slots 25 in the support members 11 intermediate the upper and lower ends thereof. The padded interior 16 of the headpiece 12 shields the patient's head fron contact with the bolts 19. The bolts 19 cooperate with the washers 20 and the bolt receiving nuts 21, which are preferably wing nuts, to secure the headpiece 12 to the support members 11 in any of various desired positions.

Referring to FIGS. 1 and 2, the device 10 is provided with a chin restrainer 23 and a forehead restrainer 24. Both of the restrainers include two separate segments secured to the headpiece 12 by an appropriate securing means such as snap rivets which can be snuggly fastened by an appropriate fastening means such as Velcro fasteners. The chin restrainer 23 and the forehead restrainer 24 cooperate to further support and immobilize the patient's head in the headpiece 12.

The device 10 is also provided with at least one support platform 18 for steadying a portion of a physician's upper limb during the performance of delicate surgical or examinational procedures. The support platform 18 is mounted to the upper end of at least one of the support members 11 and is contoured along its length to approximate the contour of the headpiece 12. However, even without the support platform 18, the upper ends of the support members 11 can be used for steadying a portion of a physician's upper limb.

Referring to FIGS. 1 and 2, the device 10 is preferably provided with two support platforms 18, which are contoured along their lengths, extending part way around the headpiece 12. The support platforms 18 are pivotably mounted to the upper ends of the support members 11. With these features, the support platforms 18 provide maximum utility and flexibility by steadying a portion of a physician's upper limb during the performance of surgical or examinational procedures on either side of the head or face.

Referring to FIGS. 1 and 3, a transverse support means 26 is provided to further support and immobilize the device 10. The transverse support means 26 includes a threaded rod 27 and a hand-grip wheel 28 which is integral with the rod 27. The rod 27 passes through both of the support members 11 and cooperates with a rod receiving nut 29. The transverse support means 26 provides means for drawing the support members 11, which are preferably slightly flexible, toward the headpiece 12 to serve as additional support for the device 10 and to serve as a further restrainer. When the transverse support means 26 is utilized, it cooperates with the construction of the headpiece 12, the chin restrainer 23 and the forehead restrainer 24 to firmly support and immobilize the patient's head in the headpiece 12.

As an alternative, the device 10 can be provided with a transverse support means having a slightly different construction. The alternative transverse support means has a threaded rod and a hand-grip wheel integral with the rod. However, the rod passes through only one of the support members and cooperates with a plate hinged to the support member adjacent the headpiece. The alternative transverse support means cooperatively advances the hinged plate toward the headpiece to serve as a further restrainer. Accordingly, when the alternative transverse support means is utilized, it, too, firmly supports and immobilizes the patient's head in the headpiece.

To use the head supporting and immobilizing device 10, the device is initially placed in a position in which the transverse support means 26 is loose and the two separate segments of both the chin restrainer 23 and the forehead restrainer 24 are unfastened. Then, the patient is placed on the support surface 14, and if desired, a pillow is placed under the patient's neck. Next, the patient's head is lowered into the headpiece 12, and the orientation of the headpiece 12 is adjusted by loosening the wing nuts 21 and sliding the bolts 19 upward or downward in the slots 25 in the support members 11. When the orientation has been adjusted, the wing nuts 21 are tightened to secure the headpiece 12 to the support members 11.

With the patient's head in the adjusted headpiece 12, the hand-grip wheel 28 of the transverse support means 26 is utilized to turn the rod 27. Then, the rod 27 cooperates with the rod receiving nut 29 to draw the support members 11 toward the headpiece 12 until they exert a slight pressure against the opposite side portions of the semi-rigid exterior 15 thereof. Next, the two separate segments of both the chin restrainer 23 and the forehead restrainer 24 are secured by snuggly fastening the fastening means. When all of the elements of the device have been tightened and secured, the patient's head is firmly supported and immobilized in the headpiece 12.

With the present invention, the patient's head is supported and immobilized in a manner in which inadvertent motion simply cannot occur to interfere with the performance of delicate surgical and examinational procedures involving the head or face. Also, even though such procedures are often quite lengthy, the patient's head is supported in a comfortable position in which the patient can breath easily and avoid undue strain. In addition, a portion of the treating physician's upper limb is steadied during the performance of such lengthy and delicate procedures. Thus, a highly useful and effective device which eliminates many of the risks normally associated with delicate surgical and examinational procedures in the area of the head and face is provided.

An alternative embodiment of the present invention is illustrated in FIGS. 4 and 5. Head supporting and immobilizing device 110 includes a single vertical support member 111 having a lower end rigidly mounted by braces 117 to a surface 114 for supporting a patient's body. The braces 117 are fashioned from the lower end of the support member 111. The device 110 also includes a headpiece 112 and means 113 for securing the headpiece 112 to the support member 111. Means 113 includes a bolt 119 which passes through a top portion of the headpiece 112. The bolt 119 also passes through a generally vertical slot 125 intermediate the upper and lower ends of the support member 111. The bolt 119 cooperates with a washer 120 and a bolt receiving nut 121, which is again preferably a wing nut, to secure the headpiece 112 to the support member 111 in any of various desired positions.

An additional feature of the alternative embodiment of the present invention is shown in FIG. 6. A support platform 118 is provided at the upper end of the support member 111 for steadying a portion of a treating physician's upper limb during the performance of delicate surgical or examinational procedures. The support platform 118 is rigidly mounted to the support member 111. The support platform 118 extends part way around the headpiece 112 and is contoured along its length in a generally semi-circular shape to approximate the contour of the headpiece 112.

Other additional features and details of the alternative embodiment of the present invention, including the features and details of the headpiece 112, are similar to those set forth above in the decription of the preferred embodiment.

While I have shown and described specific embodiments of the head supporting and immobilizing device of my invention for purposes of illustration only, it is to be understood that the invention is to be limited solely by the scope of the appended claims.

What is claimed is:

1. A head supporting and immobilizing device comprising:
   a. a headpiece having a curved upper surface shaped to approximate the contour of a patient's head and formed to receive the patient's head, said surface extending about the back, top and sides of the patient's head whereby the head is rigidly supported and immobilized, and
   b. generally vertical support means attached to said headpiece, said support means having a base adapted to affix said headpiece to a patient's body-supporting surface and having means for steadying a portion of a physician's arm.

2. The apparatus of claim 1 in which said vertical support means includes a pair of generally vertical support members.

3. The apparatus of claim 1 wherein said means for steadying includes at least one support platform mounted to an upper end of at least one of said support members for steadying a portion of said physician's upper limb.

4. The apparatus of claim 3 in which said support platform is contoured along its length to approximate the contour of said headpiece.

5. The apparatus of claim 3 including a pair of support platforms, each of said platforms being pivotably mounted to one of said support members.

6. The apparatus of claim 1 including a chin restrainer for immobilizing said patient's head in said headpiece.

7. The apparatus of claim 6 including a forehead restrainer for immobilizing said patient's head in said headpiece.

8. The apparatus of claim 2 including transverse support means for supporting and immobilizing said patient's head in said headpiece.

9. The apparatus of claim 8 in which said transverse support means includes a threaded rod extending through said support members, a hand-grip wheel integral with a first end of said rod, and a rod receiving nut which cooperates with a second end of said rod and with said hand-grip wheel to draw said support members toward said headpiece.

10. The apparatus of claim 2 in which said headpiece includes a semi-rigid exterior.

11. The apparatus of claim 10 in which said means for securing said headpiece to said support members includes a pair of bolts, each of said bolts passing through an opposite side portion of said semi-rigid exterior of said headpiece and passing through one of said support members and cooperating with a bolt receiving nut.

12. The apparatus of claim 11 in which said headpiece includes a padded interior.

13. The apparatus of claim 11 including means for adjusting the orientation of said headpiece.

14. The apparatus of claim 13 in which said means for adjusting the orientation includes a generally vertical slot in each of said support members, each of said slots disposed intermediate said upper and lower ends of said support member, and each of said bolts passing through one of said slots.

15. The apparatus of claim 13 wherein said means for steadying includes at least one support platform mounted to an upper end of at least one of said support members or steadying a portion of a physician's upper limb.

16. The apparatus of claim 15 including a chin restrainer for immobilizing said patient's head in said headpiece.

17. The apparatus of claim 16 including transverse support means for supporting and immobilizing said patient's head in said headpiece.

18. The apparatus of claim 17 in which said headpiece includes a padded interior.

19. A head supporting and immobilizing device comprising:
   a. a generally vertical support member having an upper end and a lower end rigidly mounted to a surface for supporting a patient's body;
   b. a generally semi-circular support platform rigidly mounted to said upper end of said support member;
   c. a headpiece disposed adjacent said support member and above said support surface, said headpiece adapted to receive and approximate the contour of said patient's head; and
   d. means for securing said headpiece ot said support member.

20. A head supporting and immobilizing device comprising:
   a. a headpiece having a curved upper surface shaped to approximate the contour of a patient's head and formed to receive the patient's head, said surface extending about the back, top and sides of the patient's head whereby the head is rigidly supported and immobilized,
   b. a pair of generally vertical support members horizontally spaced and attached to said headpiece, each of said support members being attached to one side of said headpiece and having a base adapted to affix said headpiece to a patient's body-supporting surface,
   c. a support platform mounted on the upper end of at least one of said support members for steadying a portion of a physician's arm, and
   d. restraining means for immobilizing the patient's head in said headpiece.

* * * * *